US00PP11356P

United States Patent [19]

Verwer

[11] Patent Number: Plant 11,356

[45] Date of Patent: Apr. 18, 2000

[54] DAHLIA PLANT NAME 'GALLERY ART FAIR'

[75] Inventor: Aad Verwer, Lisse, Netherlands

[73] Assignee: Fa. Gebr. Verwer, Lisse, Netherlands

[21] Appl. No.: 09/026,010

[22] Filed: Feb. 19, 1998

[30] Foreign Application Priority Data

Apr. 7, 1997 [NL] Netherlands ..... DHL78

[51] Int. Cl.[7] ..... A01H 5/00

[52] U.S. Cl. ..... Plt./321

[58] Field of Search ..... Plt./321

[56] References Cited

U.S. PATENT DOCUMENTS

P.P. 1,386 4/1955 Curtis et al. ..... Plt./321

OTHER PUBLICATIONS

GTITM UPOVROM Citation for 'Gallery Art Fair' as per NL PBR DHL 0078; Apr. 7, 1997.

*Primary Examiner*—Howard J. Locker
*Assistant Examiner*—Kent L. Bell
*Attorney, Agent, or Firm*—Christie, Parker & Hale, LLP

[57] ABSTRACT

A compact growing, continuously flowering perennial dehlia plant producing white flowers.

1 Drawing Sheet

BACKGROUND OF THE INVENTION

The present invention relates to a new and distinct variety of Dahlia hybrida known by the varietal denomination 'Gallery Art Fair'. 'Gallery Art Fair' is the result of open pollination of the variety known as 'Aspen' (unpatented) as female parent, male parent not known.

SUMMARY OF THE INVENTION

The new variety is a dahlia plant with low growing habit which produces attractive white flowers against a background of abundant medium green foliage. The continuous flowering perennial plant is compact and suitable for use as a pot plant and for outdoor gardens. Inflorescence is compact and extends above the foliage with flowers borne on relatively short peduncles. Plant height is about 25 cm. Roots of cuttings of the new variety are initiated in about 6 days at 20° C and a rooted cutting is produced in about 14 days at 20° C. The rooting habit is such that fine roots are produced first and then become fleshy. Among the traits possessed by the new variety which in combination distinguish it from other varieties known to the inventor are its compact plant habit and flower color and continuous flowering during the growing season.

Asexual reproduction by cuttings of the new variety in The Netherlands has demonstrated that the combination of characteristics as described herein for 'Gallery Art Fair' are firmly fixed and are retained through successive generations of asexual reproduction.

COMPARISON WITH PARENT

The new variety differs from its parent 'Aspen' in shape of flowers (more decorative) and plant (larger, more branching) as well as foliage color (deeper green).

BRIEF DESCRIPTION OF ILLUSTRATION

The accompanying color photographic illustration shows a typical plant of the new variety in colors as nearly true as possible with an illustration of this type. The illustration depicts growth habit, flower position relative to leaves and flower color.

DESCRIPTION OF THE NEW VARIETY

In the following description, color references are to The Royal Horticultural Society Colour Chart, where color values refer to color plate numbers in this chart.

The following observations are of plants described and grown in The Netherlands under greenhouse and outdoor conditions which approximate those generally used in commercial practice.

'Gallery Art Fair' has not been observed under all possible environmental conditions. The phenotype may vary with variations in environment such as temperature, light intensity, day length and cultural conditions.

Parentage: Open pollination of the variety 'Aspen' as female parent.

Growing conditions: Useful growing conditions include day temperatures of about 15° to 22° C. and night temperature about 10° to 15° C. with normal daylight about 14 hours. Plants grow normally June to September in The Netherlands. No growth regulator treatments are required.

Plant:

*Plant shape.*—Rounded.
*Growth habit*—Spreading, upright.
*Height.*—About 25 cm.
*Growth rate.*—Rapid.
*Branching characteristics.*—Freely branching.
*Vigor.*—Vigorous.
*Crop time.*—About 50 to 60 days.
*Hardiness.*—Plants are winter hardy to 0° C.
*Disease resistance.*—Similar to the species.

Foliage:

*Arrangement.*—Opposite.
*Type.*—Compound and single.
*Leaves.*—Quantity of leaves: Many. Leaflets: Compound 3 and 5. Length: Single, about 10 cm; compound about 20 cm. Width: Single about 3.3 cm, compound 17 cm. Shape: Ovate. Tip: Acute. Base: Cordate. Attachment: Stalked.
*Petiole length.*—Compound, about 7 cm.
*Margin.*—Dentate.
*Texture.*—Leathery.
*Pubescence upper side; and underside.*—Absent.
*Color.*—Young foliage: Upperside near 137A; under side near 148B. Mature foliage: Upperside near 137A; under side near 148B. Petiole: near 148A, with anthocyanin coloration. Venation: Upperside near 148B; under side near 146B.

*Venation.*—Pinnate.

Flower:

*Habit.*—Recurrent, continuous during season.

*Form.*—Decorative, double.

*Natural flowering season.*—Summer to Autumn.

*Quantity of flowers per stem.*—Usually 1.

*Diameter.*—About 110 mm.

*Depth.*—About 40 mm.

*Longevity on plant.*—About 10 to 14 days.

*Longevity as cut flower.*—About 6 to 7 days.

*Persistent or self-cleaning.*—Not self-cleaning.

*Fragrance.*—None.

*Ray florets.*—Number: About 200. Appearance: Shiny, satiny. Texture: Smooth. Arrangement: In rows around the center of the capitulum. Shape: Oblanceolate. Margin: Entire. Tip: Obtuse. Base: Rounded. Length: About 48 mm. Width: About 20 mm. Color: When opening: Near 155C. Upperside: Near 155C; at base near 1A. Under side: Near 155C. After senescence: Near 159B.

*Disc florets.*—Number: About 25. Length: About 1.3 cm. Color: Near 10A. Shape: Cylinric.

*Peduncle or flower stem.*—Length: About 20 to 22 cm. Color: Near 144D. Strength: Strong. Angle: Erect. Pubescence: None.

*Bud.*—Length: About 10 mm. Diameter: About 12 mm. Shape: Globular. Rate of opening: Opens in about 14 days. Color: Near 151A.

*Sepals.*—Appearance: Satiny. Texture: Smooth. Arrangement: In circle, around stem. Number: About 20. Length: About 2.2 cm. Width: About 1.5 cm. Shape: Ovate. Margin: Entire. Tip: Rounded. Base: Rounded. Color: Upperside near 137A; under side near 137A.

*Stamens.*—Number: Many. Anther shape: Long, pointed. Anther size: Small. Anther color: Near 16A. Pollen color: Near 17A.

*Pistils.*—Number: Many. Stigma shape: Divided, two. Stigma color: Near 14A. Style color: Near 154B. Style length: About 3 mm. Ovary number: 1 per pistil.

I claim:

1. A new and distinct dahlia plant of the variety substantially as shown and described.

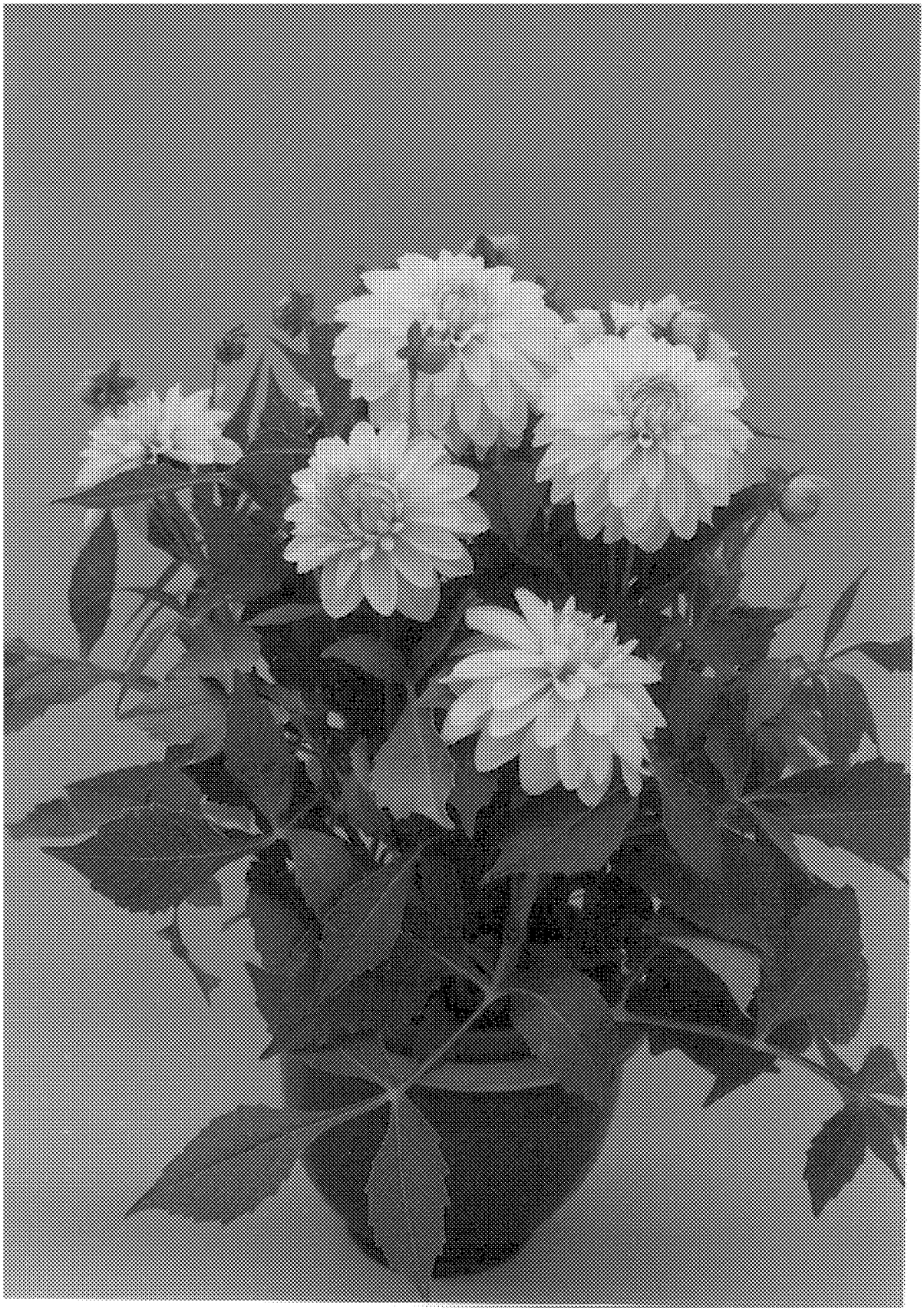

* * * * *